US009706931B2

(12) United States Patent
Fuke et al.

(10) Patent No.: US 9,706,931 B2
(45) Date of Patent: Jul. 18, 2017

(54) BIOSIGNAL MEASURING DEVICE, BIOSIGNAL MEASURING METHOD AND BIOSIGNAL PROGRAM

(71) Applicant: TDK Corporation, Tokyo (JP)

(72) Inventors: Sawa Fuke, Kanagawa (JP); Takuji Suzuki, Kanagawa (JP); Kanako Nakayama, Tokyo (JP)

(73) Assignee: TDK Corporation, Tokyo (JP)

( * ) Notice: Subject to any disclaimer, the term of this patent is extended or adjusted under 35 U.S.C. 154(b) by 640 days.

(21) Appl. No.: 13/774,370

(22) Filed: Feb. 22, 2013

(65) Prior Publication Data
US 2014/0142441 A1    May 22, 2014

(30) Foreign Application Priority Data
Nov. 19, 2012   (JP) ................................. 2012-253549

(51) Int. Cl.
*A61B 5/0402*   (2006.01)
*A61B 5/021*    (2006.01)
(Continued)

(52) U.S. Cl.
CPC ........ *A61B 5/02108* (2013.01); *A61B 5/0285* (2013.01); *A61B 5/04012* (2013.01); *A61B 5/0295* (2013.01); *A61B 5/0402* (2013.01)

(58) Field of Classification Search
CPC ... A61B 5/0402; A61B 5/0205; A61B 5/0452; A61B 5/021; A61B 5/0456;
(Continued)

(56) References Cited

U.S. PATENT DOCUMENTS 6,331,162 B1 *  12/2001  Mitchell ....................... 600/485
8,428,673 B2 *   4/2013  Cho et al. ..................... 600/323
(Continued)

FOREIGN PATENT DOCUMENTS

JP    3054084 B2    2/1998
JP    4795731 B2    1/2007

*Primary Examiner* — Christopher D Koharski
*Assistant Examiner* — Jeremiah Kimball
(74) *Attorney, Agent, or Firm* — Patterson & Sheridan, LLP (57) ABSTRACT

A biosignal measuring device has a first information acquisition module, a second information acquisition module, a first calculation module, a second calculation module, a third calculation module, a heartbeat interval estimation module, a determination module, and an output module. The first information acquisition module acquires the pulse wave signal. The second information acquisition module acquires an electrocardiogram signal. The first calculation module calculates a pulse wave velocity based. The second calculation module determines a heartbeat interval. The third calculation module calculates a relationship between pulse wave velocity and the heartbeat interval. The heartbeat interval estimation module estimates an estimated heartbeat interval based on pulse wave velocity and calculated relationship. The determination module determines whether the position of the first and second information acquisition modules has changed based on the heartbeat interval and the estimated heartbeat interval. The output module outputs information.

20 Claims, 5 Drawing Sheets

(51) Int. Cl.
*A61B 5/04* (2006.01)
*A61B 5/0285* (2006.01)
*A61B 5/0295* (2006.01)

(58) Field of Classification Search
CPC ... A61B 5/0245; A61B 5/04012; A61B 5/024;
A61B 5/0006; A61B 5/029; A61B 5/742;
A61B 5/1118; A61B 5/02416; A61B
5/026; A61B 5/0408; A61B 5/02438;
A61B 5/04085; A61B 5/02; A61B
5/0295; A61B 5/0261; A61B 5/7246;
A61B 5/6823; A61B 5/7221; A61B
5/02108; A61B 5/6824; A61B 5/721;
A61B 5/02116; A61B 5/04087; A61B
5/7405; A61B 5/74; A61B 5/36585
USPC .......................................................... 600/513
See application file for complete search history.

(56) References Cited

U.S. PATENT DOCUMENTS

| | | | |
|---|---|---|---|
| 9,060,700 B2* | 6/2015 | Cho et al. | 600/301 |
| 2005/0090720 A1* | 4/2005 | Wu et al. | 600/300 |
| 2007/0276262 A1* | 11/2007 | Banet et al. | 600/485 |
| 2009/0082681 A1* | 3/2009 | Yokoyama et al. | 600/509 |
| 2009/0204011 A1* | 8/2009 | Suzuki | 600/500 |
| 2009/0281399 A1* | 11/2009 | Keel et al. | 600/301 |
| 2010/0004546 A1* | 1/2010 | Tanaka et al. | 600/485 |
| 2010/0228311 A1* | 9/2010 | Naqvi et al. | 607/18 |
| 2012/0179053 A1* | 7/2012 | Gemignani et al. | 600/485 |
| 2013/0018272 A1* | 1/2013 | Hori | 600/501 |
| 2013/0109982 A1* | 5/2013 | Sato et al. | 600/502 |

* cited by examiner

BIOSIGNAL MEASURING DEVICE, BIOSIGNAL MEASURING METHOD AND BIOSIGNAL PROGRAM

CROSS-REFERENCE TO RELATED APPLICATION

This application is based upon and claims the benefit of priority from Japanese Patent Application No. 2012-253549, filed Nov. 19, 2012; the entire contents of which are incorporated herein by reference.

FIELD

Embodiments described herein relate to a biosignal-measuring device, a biosignal measuring method, and a biosignal-measuring program.

BACKGROUND

Conventionally, it has been known that there is a correlation between pulse wave velocity or time, calculated from the pulse waveform or the electrocardiographic waveform measured at two points, and blood pressures. Therefore, there have been developed methods in which a sensor device attached to the body of a subject measures the pulse wave velocity and estimates the blood pressure continuously with the purpose of maintaining the physical condition and health, or catamnestic observation. Currently, biosignal-measuring devices for measuring the pulse wave and the electrocardiogram signals are being miniaturized and made to communicate wirelessly. In the future, it is expected biosignal-measuring devices may be worn continuously by a subject in daily life, and the biosignal-measuring device will estimate blood pressure, or the like, continuously over a long period by determining such things as the pulse wave velocity from the pulse wave signal and/or an electrocardiogram.

But it is expected that when a signal device is continuously worn in daily life the signal measuring device may move or be moved on occasion and such movement may prevent or interrupt the continuous measurement process, and thus render the signal measuring device inoperative or otherwise lessen the utility of such a signal measuring device.

In the continuous measurement or calculation of a biosignal such as blood pressure, if the obtained value varies significantly or the obtained value deviates from a specified range, it may be possible to determine that an abnormal event occurred. However, if the measurement is suspended temporarily, sometimes it is not possible to determine whether the significant variation of the measured or calculated value, or deviation from the specified range is caused by the variation of the targeted biosignal or by the change in a condition such as the measuring position.

DETAILED DESCRIPTION

Embodiments of the present disclosure provide a biosignal-measuring device, a biosignal-measuring method, and a biosignal-measuring program that allow the appropriate measurement of a biosignal even when the measuring position of the biosignal changes.

The biosignal-measuring device of an embodiment has a first information acquisition module, a second information acquisition module, a first calculation module, a second calculation module, a third calculation module, a heartbeat interval estimation module, a determination module, and an output module. The first information acquisition module detects a pulse wave signal from a subject. The second information acquisition module detects an electrocardiogram signal or a pulse wave signal at a different position than the first information acquisition module. The first calculation module calculates the pulse wave velocity based on the acquired result of the first information acquisition module and the second information acquisition module. The second calculation module calculates the heartbeat interval based on the acquired result of the first information acquisition module or the second information acquisition module. The third calculation module calculates a relational expression between the pulse wave velocity and the heartbeat interval. The heartbeat interval estimation module estimates the estimated heartbeat interval based on the pulse wave velocity and the relational expression. The determination module determines whether or not the position of at least one of the first information acquisition module or the second information acquisition module has changed. The output module outputs the information based on the result determined by the determination module.

A systolic blood pressure P can be estimated by, for example, the equation 1 below, based on a hemodynamic model. Here, the pulse wave velocity is c, the Young's modulus of the vascular wall is $E_0$, the parameter relating to variation in the Young's modulus is a constant $\zeta$, the diameter of the blood vessel is R, the thickness of the vascular wall is h, and a blood property is $\rho$.

Equation 1

$$P = \frac{1}{\zeta}\ln(c^2) - \frac{1}{\zeta}\ln\left(\frac{hE_0}{2R_\rho}\right) = \alpha\ln(c^2) + \beta \qquad (1)$$

Also, there is a confirmed correlation between the blood pressure value and the pulse wave velocity itself. The initial values of coefficients $\alpha$ and $\beta$ are pre-determined by measuring a blood pressure value using a cuff sphygmomanometer (or other standard measurement device) along with the pulse wave velocity.

The relation between the pulse wave velocity and the blood pressure varies according to such things as the distance of blood vessels between the measuring points of the pulse wave and the electrocardiogram, the elasticity of the vascular wall, and the diameter of the blood vessel. Therefore, in the case the blood pressure value is estimated continuously from the pulse wave velocity, it is preferable to measure the pulse wave, the electrocardiogram, and the like under the same conditions without changing the measuring positions for the pulse wave and the electrocardiogram.

For example, in the case the subject measures a pulse wave and electrocardiogram continuously by wearing a biosignal-measuring device, sometimes the measuring points of the pulse wave and the electrocardiogram may slide (slip) or change. If the measuring points of the pulse wave and the electrocardiogram slide, appropriate measuring of the biosignal becomes impossible because of the changes in the measuring conditions.

Figure 1:
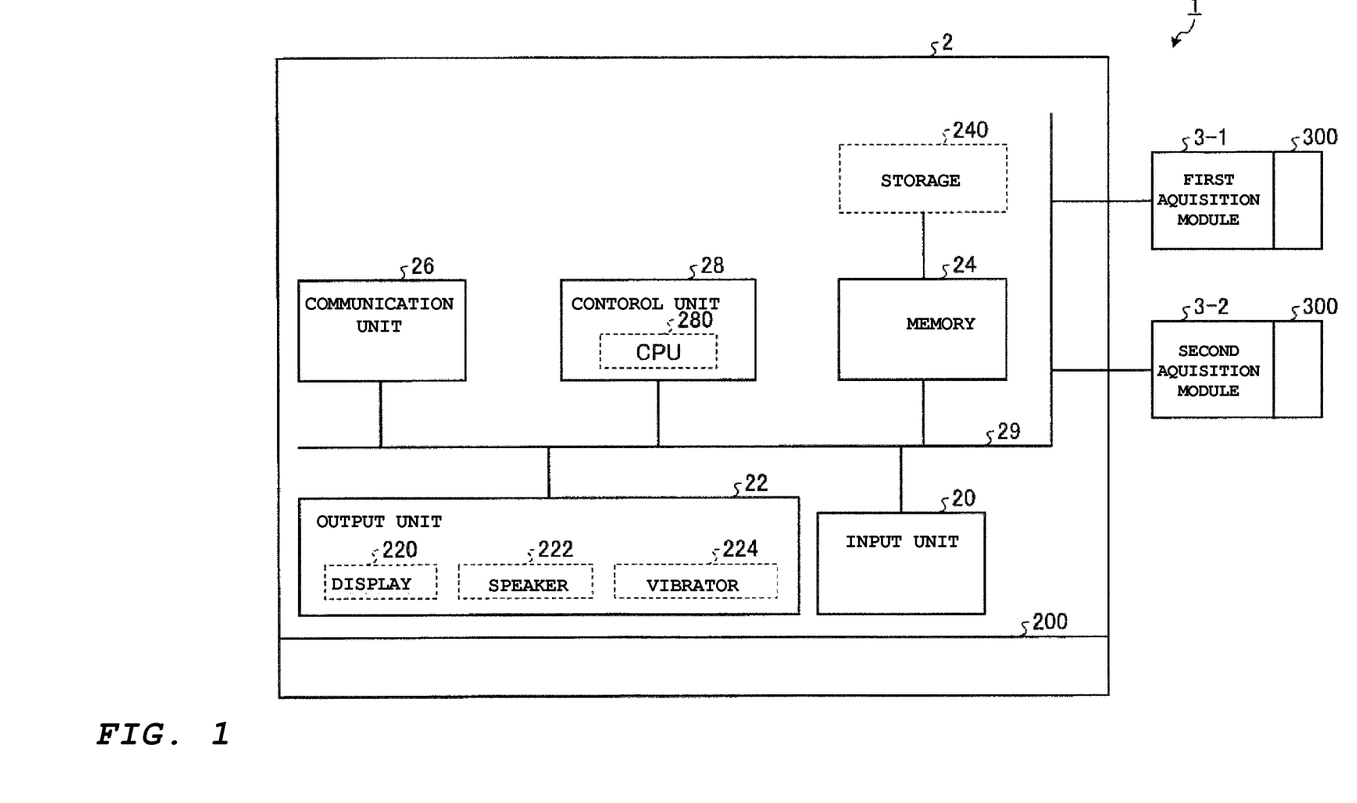
FIG. 1 is a block drawing showing an example of the hardware configuration of a biosignal-measuring device according to an embodiment.

In order to take an appropriate measurement of the biosignal continuously, in the case measuring points slide and the measuring condition therefore changes, it is necessary to output a notice urging the subject (or an attendant) to move the measuring point back to the original positions. It is also effective to recalibrate the biosignal measuring device according to the slippage of the measuring position, or to correct the measured results according to the changes in the measuring condition. The biosignal measuring device of an embodiment determines whether or not the measuring point of the biosignals has changed. In the following, an embodiment of a biosignal-measuring device will be explained in detail with reference to the attached drawings. FIG. 1 is a block drawing exemplifying the hardware configuration of a biosignal-measuring device 1 according to an embodiment. As shown in FIG. 1, the biosignal-measuring device 1 has a body unit 2, a first information acquisition module 3-1 and a second information acquisition module 3-2.

For example, the body unit 2 is attached to a mounting unit 200 such as a belt to be placed around the waist area, and the like of a subject. The mounting unit 200 attaches the body unit 2 to the subject for measuring the biosignals. A mounting part 300 is installed on each of the first information acquisition part 3-1 and the second information acquisition module 3-2. The mounting module 300 is, for example, an adhesive material. The mounting part 300 adheres each of the first information acquisition module 3-1 and the second information acquisition module 3-2 on the body of the subject on which the biosignal measurement is to be made. In the case of the body unit 2, the first information acquisition module 3-1 and the second information acquisition module 3-2 are integrated, the mounting part 300 with an adhesive material, or the like, may serve an equivalent function as the mounting unit 200.

The first information acquisition module 3-1 has, for example, photoplethysmogram sensor with a sampling frequency of 1,000 Hz. The first information acquisition module 3-1 in this example would shine light on capillary vessels beneath the body surface from a light emitter not shown in the drawing. The first information acquisition module 3-1 receives the reflected light from the capillary vessels with photo detectors. The amount of reflected light depends on the volume of the blood vessel and the volume of the blood vessel changes according to blood flow. The first information acquisition module 3-1 acquires the pulse wave (pulse wave signal) of the capillary vessels beneath the body surface. The second information acquisition module 3-2 has, for example, the same photoplethysmogram sensor as the first information acquisition module 3-1, or an electrocardiogram sensor with the sampling frequency of, for example, 1,000 Hz.

Figure 2:
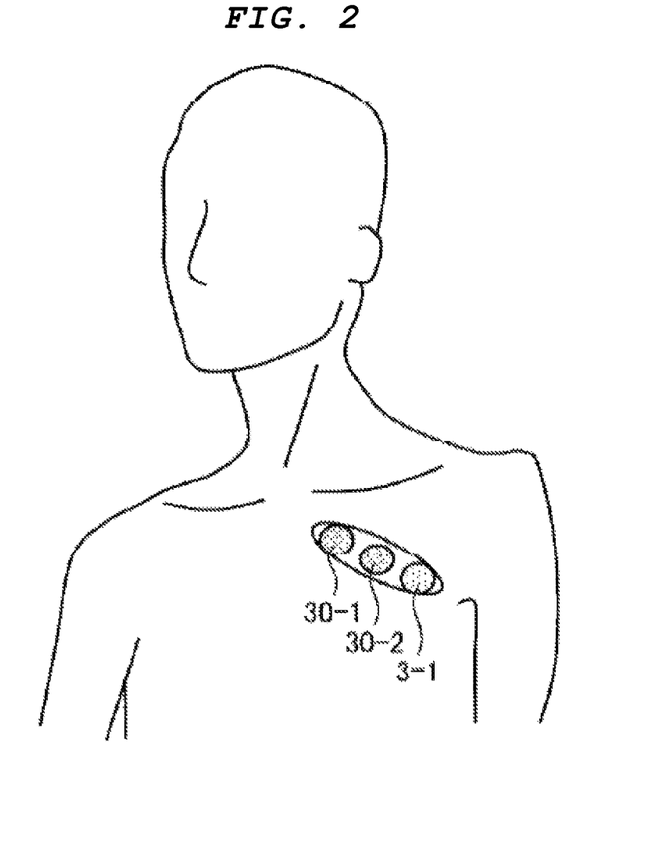
FIG. 2 is a schematic drawing showing an example in which the first information acquisition unit and the second information acquisition unit are attached to the body of a subject.

FIG. 2 is a schematic drawing in which the first information acquisition module 3-1 and the second information acquisition module 3-2 are attached to the subject. The second information acquisition module 3-2 has, for example, electrodes 30-1 and 30-2 for an electrocardiogram measurement. The electrodes 30-1 and 30-2 can be adhered to the subject, and used to acquire the electrocardiographic waveform (electrocardiogram signal). The first information acquisition module 3-1 is adhered to the subject in such a way as the distances between the first information acquisition module 3-1 and the electrodes 30-1 and 30-2 are predetermined. Here, the first information acquisition module 3-1 and electrodes for the electrocardiogram 30-1 and 30-2 can have an integrated configuration as long as they can be attached to the subject with a predetermined spacing.

The body unit 2 (FIG. 1) has an input module 20, an output module 22, a memory module 24, a communication unit 26, and a control unit 28. Each part including the body unit 2 is connected to the others through a bus 29. Also, the first information acquisition module 3-1 and the second information acquisition module 3-2 are connected to the bus 29.

The input module 20 is, for example, an input key or a switch or the like, and receives input from the subject. The output module 22 has a display unit 220, such as a liquid display panel, a speaker 222 to output sounds and a vibration unit 224 to generate vibration. The output module 22 displays the results, and the like of processing operations, and can output sounds and vibrations. Also, the input module 20 and the display unit 220 can be integrated as a touch panel display, or the like.

The memory module 24 includes ROM (Read Only Memory) and RAM (Random Access Memory), not shown in the drawing, and stores a program that control unit 28 executes and the data that control unit 28 uses in executing the program. Also, a storage medium 240, such as a memory card, in which programs and data can be stored and sent to and received from the memory module 24 may optionally included in the body unit 2. Such storage medium 240 may be freely removable from the body unit 2, or may be permanently integrated The communication unit 26 may be an all-purpose interface to communicate with external devices, and performs, for example, cable broadcasting communication, long-distance wireless communication, or proximity wireless communication. The communication unit 26 can receive the input operation of the subject by conducting a wireless communication with an external apparatus, and receiving input commands from the external apparatus instead of by operation of the input module 20. The communication unit 26 can also output the result of the processing operations to the external apparatus by conducting a wireless communication with the external apparatus and sending the result of the processed operation to the external apparatus rather than outputting the result to the output module 22.

The control unit 28 includes, for example, a CPU 280, and controls the various modules and units including the biosignal-measuring device 1.

Figure 3:
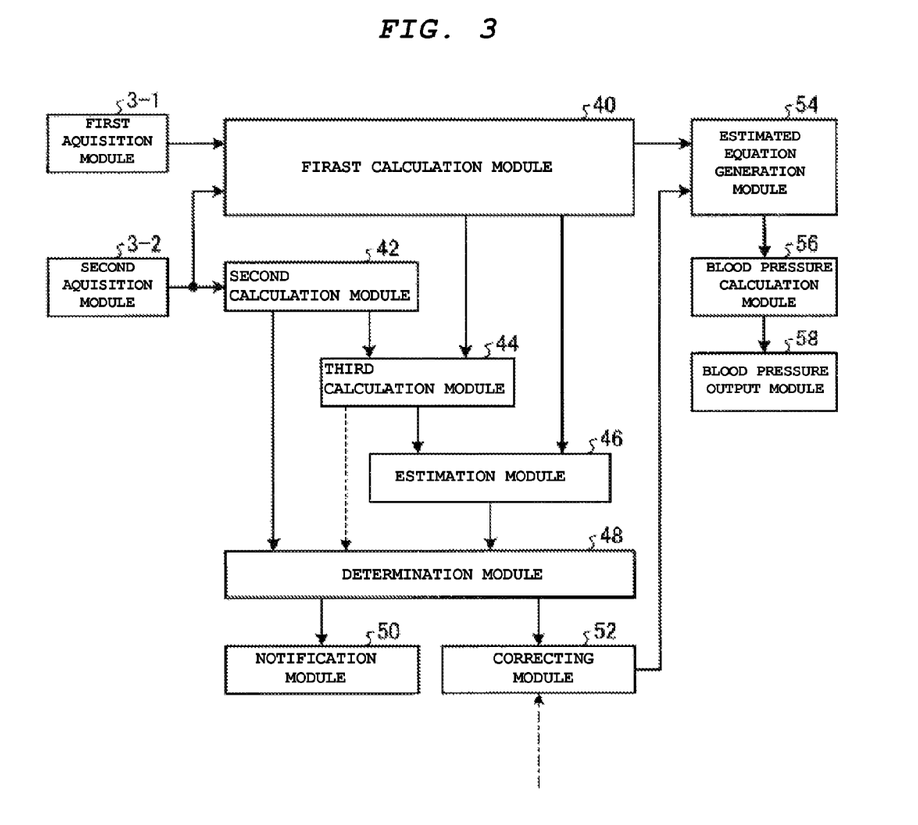
FIG. 3 is a block diagram of a biosignal-measuring device according to an embodiment.

Next, the operation of the biosignal-measuring device 1 will be explained. FIG. 3 is a block diagram of a biosignal-measuring device 1 according to an embodiment.

As shown in FIG. 3, the biosignal-measuring device 1 has a first information acquisition module 3-1, a second information acquisition module 3-2, a first calculation module 40, a second calculation module 42, a third calculation module 44, a heartbeat interval estimation module 46, a determination module 48, a notification section 50, a correcting module 52, an estimated equation generation module 54, a blood pressure calculation module 56 and a blood pressure output module 58. Here, the first information acquisition module 3-1 and the second information acquisition module 3-2, shown in FIG. 3, correspond to the first information acquisition module 3-1 and the second information acquisition module 3-2 depicted in FIG. 1.

The first calculation module 40 receives the pulse wave acquired by the first information acquisition module 3-1, and the electrocardiographic waveform acquired by the second information acquisition module 3-2, and calculates the pulse wave velocity or the feature value of the pulse wave velocity (in this example, the feature value is ln (pulse wave velocity$^2$)). In more detail, the first calculation module 40 implements a filter to the pulse wave and the electrocardiographic waveform, continuously calculates the pulse wave velocity from such featured points as the peak time of R-wave in the electrocardiographic waveform and the onset time of the pulse wave waveform, and then calculates the feature value of the pulse wave velocity. And the first calculation module 40 outputs the calculation result to the third calculation module 44, the heartbeat interval estimation module 46, and the estimated equation generation module 54.

The second calculation module 42, for example, receives the electrocardiographic waveform acquired by the second information acquisition module 3-2, and continuously calculates the heartbeat intervals. In more detail, the second calculation module 42 calculates the time interval of a specific point such as the peak of the R-wave as a heartbeat interval. Here, in the case the second information acquisition module 3-2 detects the pulse wave signal, the second calculation module 42 calculates the period of pulse wave, which is the time interval of specific points of the pulse wave waveform. And the second calculation module 42 outputs the calculated result to the third calculation module 44 and the determination module 48. In the following, the heartbeat intervals calculated by the second calculation module 42 may be called the calculated heartbeat intervals.

The third calculation module 44 receives the feature value of the pulse wave velocity calculated by the first calculation module 40 and the calculated interval calculated by the second calculation module 42, and calculates the relational expression between the pulse wave velocity and the calculated intervals in a specified interval. The specified interval means a certain period of time during which the third calculation module 44 estimates that there is little noise caused by subject's body movement and impact, and that the biosignal is stably received. For example, the third calculation module 44 estimates, as the specified interval, the interval in which the first peak outputs of an autocorrelation function computed from the pulse wave is over a specified threshold and a high periodicity is confirmed, and in which the high frequency amplitude caused by the muscle potential in the electrocardiographic waveform is under a specified threshold.

Here, the third calculation module 44 can estimate the specified interval by further receiving the acceleration signal from an acceleration sensor, not shown in the drawing, installed in the biosignal-measuring device 1, and estimating the motion stability of the living body according to the acceleration signal detected by the sensor. Also, the third calculation module 44 may be configured so that the interval set through the input module 20 (FIG. 1) is the specified interval.

Figure 4:
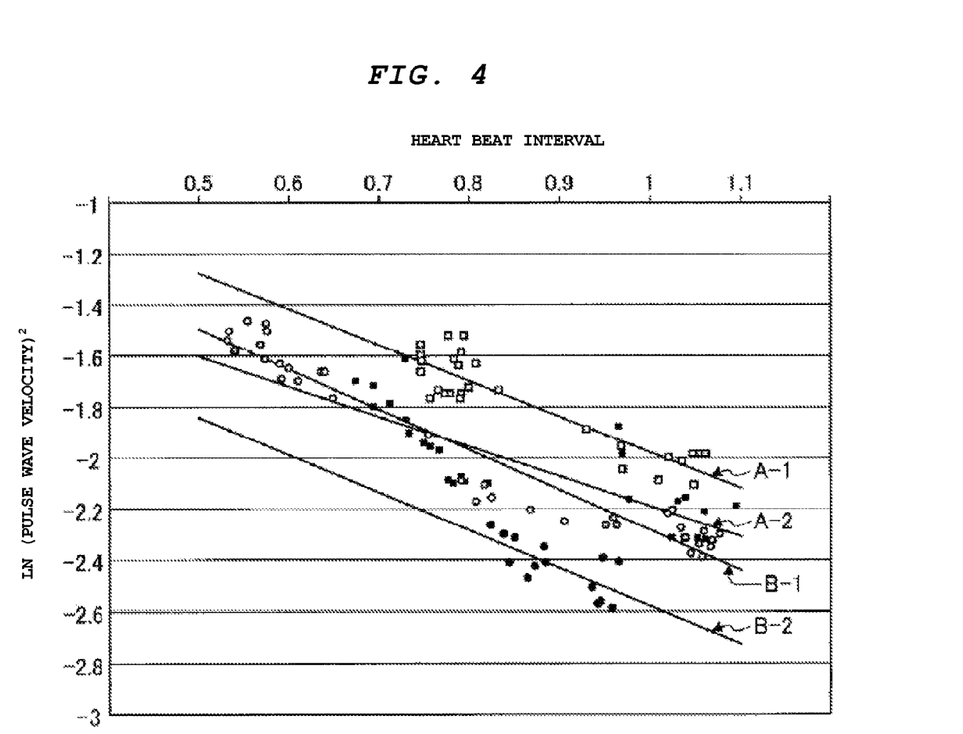
FIG. 4 is a graph depicting the relation between the heartbeat interval and the feature value of the pulse wave velocity calculated by a third calculation unit.

FIG. 4 is a graph depicting the relational expression between the feature value of the pulse wave velocity and the heartbeat interval calculated by the third calculation module 44. For example, the third calculation module 44 calculates the relational expression of the feature value of the pulse wave velocity and the heartbeat interval by the least-squares method as a regression line. FIG. 4 is a graph showing, for each of the subjects A and B, the relational expressions between the cases in which the first information acquisition module 3-1 and the second information acquisition module 3-2 are attached in the chest area and attached in the epigastrium.

FIG. 4 shows the relational expressions taking the calculated heartbeat interval on the horizontal axis and the pulse wave velocity feature value (ln (pulse wave velocity)$^2$) on the vertical axis. The relational expression of subject A in the epigastrium is shown in A-1, and in the chest area is shown in A-2, while the relational expression of subject B in the epigastrium is shown in B-1, and in the chest area is shown in B-2.

For example, the correlation coefficient between the heartbeat interval and the feature value of the pulse wave velocity in the chest area of subject A is −0.924. Also, the correlation coefficient between the heartbeat interval and the feature value of the pulse wave velocity in the epigastrium of subject A is −0.873. As depicted, there is a strong correlation between the feature value of the pulse wave velocity and the calculated heartbeat interval for each subject and each measuring point.

Here, the third calculation module 44 is not limited to calculating the relational expression by the least-squares method. For example, the third calculation module 44 can calculate by other regression models such as neural network regression.

And the third calculation module 44 outputs the relational expression to the interval estimation module 46, and stores the expression in the memory module 24. For example, the third calculation module 44 outputs the parameters of the relational expression (e.g., the slope and the intercept of the regression line shown in FIG. 4) to the heartbeat interval estimation module 46 and the memory module 24.

Here, the third calculation module 44 has an initial value (or the set value of the relational expression) of the parameters of the relational expression. Also, the heartbeat interval estimation module 46 can be configured to set the initial value of the parameters of the relational expression corresponding to the signal from outside. Also, the third calculation module 44 can be configured to output to the determination module 48 a maximum error value and variance, and the like between the expected value and the actual measurement value used in calculating the relational expression.

The heartbeat interval estimation module 46 estimates the heartbeat interval using the pulse wave velocity received from the first calculation module 40 and the relational expression received from the third calculation module 44. And the heartbeat interval estimation module 46 outputs the estimated heartbeat interval to the determination module 48. In the following, the heartbeat interval estimated by the heartbeat interval estimation module 46 is sometimes called the "estimated heartbeat interval."

The determination module 48 receives the estimated heartbeat interval from the heartbeat interval estimation module 46, receives the calculated heartbeat interval from the second calculation module 42, and determines whether or not at one or both of the positions of the first information acquisition module 3-1 or the second information acquisition module 3-2 has changed. In other words, the determination module 48 determines whether or not the attached positions of the first information acquisition module 3-1 and the second information acquisition module 3-2 slipped.

In more detail, the determination module 48 determines that an abnormal event has occurred (e.g., slippage occurred in the attached position of the first information acquisition module 3-1 or the second information acquisition module 3-2) which has caused a change in measuring conditions. The determination module 48 can determine the abnormal event has occurred if the difference between the calculated heartbeat period and the estimated heartbeat period is continuously over a predetermined threshold value for a specified period. Also, the determination module 48 can determine that no change in measuring conditions occurred if the difference between the calculated heartbeat interval and the estimated heartbeat interval is below the threshold. The determination module 48 outputs the determined result to the notification module 50 and the correcting module 52. Here the determination module 48 can also be configured not to determine that an abnormal event has occurred even if the difference between the calculated heartbeat interval and the heartbeat interval is over the threshold, if the heartbeat interval estimation module 46 estimates the estimated heartbeat interval using the relational expression to which the initial parameter values are applied.

Here, each threshold used by the determination module 48 does not have to be predetermined. For example, the determination module 48 can be configured to update threshold upon receiving the maximum error value and the variance between the estimated value of the heartbeat interval and the measured value of the interval used in the calculation of the relational expression calculation by the third calculation module 44.

The notification section 50 includes an output module 22 or the communication unit 26 or similar structure. The notification section 50 sends notice to the subject (and potentially others) that the position of the first information acquisition module 3-1 or the second information acquisition module 3-2 has slipped if it receives the determination result from the determination module 48 showing that the position of the first information acquisition module 3-1 or the second information acquisition module 3-2 has slipped.

To be precise, the notification section 50 outputs a notice by a display, a sound, or a vibration by the output module 22, or through communication by the communication unit 26, to the subject (and potentially others). The notice urges the subject (or others) to change the position of the first information acquisition module 3-1 or the second information acquisition module 3-2 back to the original position. It is also possible to recalibrate the biosignal-measuring device 1 corresponding to the slippage of the measuring position, or to correct the measured results corresponding to the change in measuring conditions, when the notification section 50 sends a notice showing that the attached position of the first information acquisition module 3-1 or the second information acquisition module 3-2 has slipped.

The correcting module 52 corrects the relational expression, for example, between the feature value of the pulse wave velocity and the blood pressure (such as parameters $\alpha$ and $\beta$ in the above Equation 1) stored in the memory module 24, and outputs the correction result to estimate the equation generation module 54, if the correcting module 52 receives the determination result from the determination module 48 indicating that a change occurred in measuring conditions. Here, the correction module 52 can correct the relational expression responding to the setting input from outside through such part as the input module 20 or the communication unit 26 (FIG. 1), or correct the relational expression according to multiple data stored in the memory module 24, and the like in advance.

For example, in case the measuring condition changes, the subject measures his/her blood pressure again with a cuff sphygmomanometer and the correcting module 52 makes corrections to the relational expression (parameters $\alpha$ and $\beta$, and the like in the above Equation 1) between the feature value of the pulse wave velocity and the blood pressure according to the new measurement result.

If the pulse wave velocity is fast even if the heartbeat period or the heart rate is the same (In FIG. 4, for both subjects, the pulse wave velocity is greater in the chest area than in the epigastrium), possible causes may be that the diameter of the measured capillary vessel beneath the surface is small, that the Young's modulus of the vascular wall is high, or that the vascular wall is thick, and so on.

Coefficient "$\beta$" in the above equation 1 also varies depending on the diameter of the blood vessel, the Young's modulus and the thickness of the vascular wall, so it can be updated according to the parameters of the relational expression calculated by the third calculation module 44.

Also, there can be a configuration in which the correction module 52 stores (e.g., in memory module 24) $\alpha$ and $\beta$ that are previously calculated for each condition and then selects $\alpha$ and $\beta$ according to the corresponding conditions. Here, the correction module 52, for example, does not correct when the determination result showing that there has been no change in the measuring condition is received from the determination module 48.

The estimated equation generation module 54 receives the calculation result of the first calculation module 40, and generates the estimated equation (the above Equation 1) of the systolic blood pressure value P to which the calculated pulse wave velocity is applied. Also, the estimated equation generation module 54, in the case it receives the result in which the correction module 52 corrected the relational expression, generates the above Equation 1 to which the corrected result is applied. And the estimated equation generation module 54 outputs the generated estimated equation to the blood pressure calculation module 56.

The blood pressure calculation module 56 calculates the systolic blood pressure value P, using the estimated equation for the systolic blood pressure P received from the estimated equation generation module 54, and outputs the calculation result to the blood pressure output module 58.

The blood pressure output module 58 includes the output module 22 and/or the communication unit 26. And the blood pressure output module 58 outputs the calculation results of the systolicblood pressure P received from the blood pressure calculation module 56 through display by the output module 22, a sound, or a vibration, or communication by the communication unit 26.

Figure 5:
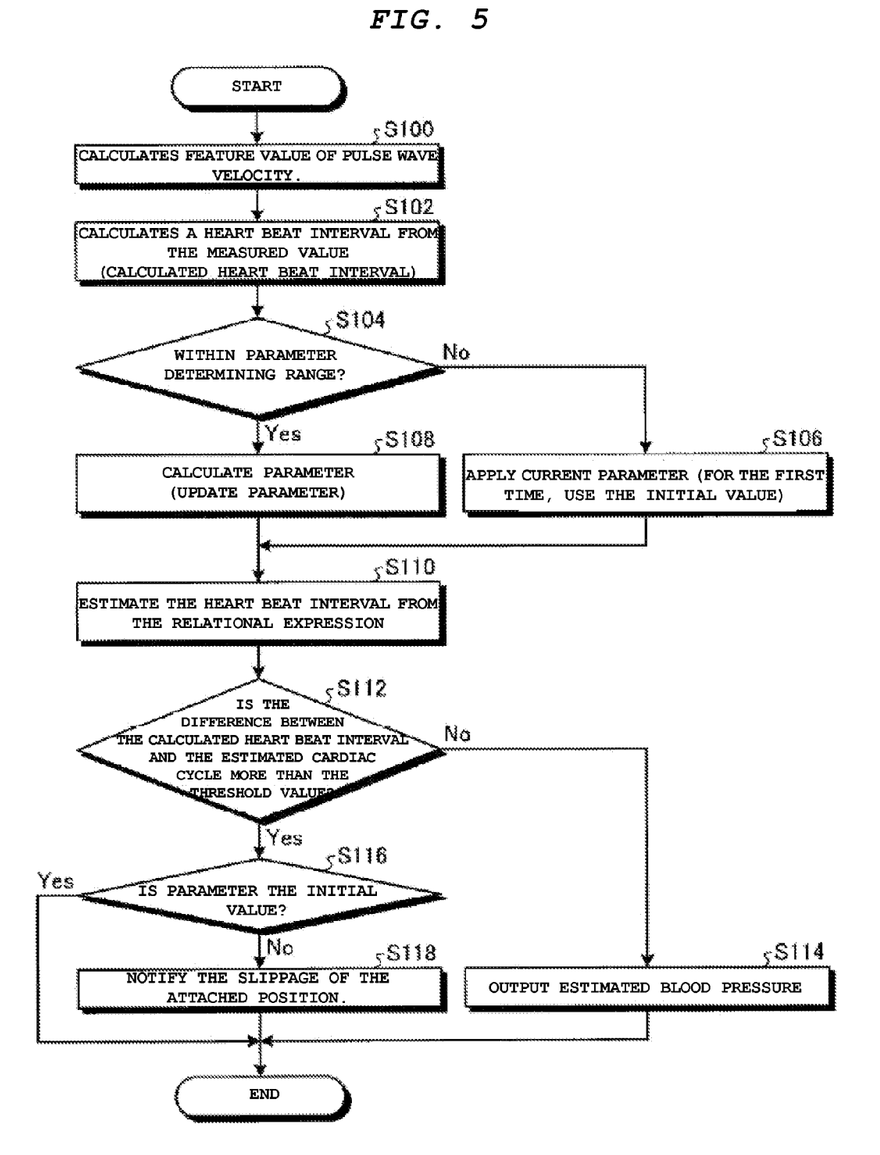
FIG. 5 is a flow chart illustrating an operation of the biosignal-measure device according to an embodiment.

Next, the operation of the biosignal-measuring device 1 will be explained. FIG. 5 is a flow chart showing an example of the operation of the biosignal-measuring device 1 of according to an embodiment. The biosignal-measuring device 1, for example, continuously estimates the blood pressure of the subject by continuously executing the operation shown in the flow chart in FIG. 5.

At step 100 (S100), the first calculation module 40 receives a pulse wave acquired by the first information acquisition module 3-1 and an electrocardiographic waveform acquired by the second information acquisition module 3-2, then calculates the pulse wave velocity and the corresponding feature value of the pulse wave velocity.

At step 102 (S102), the second calculation module 42 receives the electrocardiographic waveform (the measured value) acquired by the second information acquisition module 3-2, and calculates the heartbeat interval (calculated heartbeat interval).

At step 104 (S104), the third calculation module 44 receives the feature value of the pulse wave velocity calculated by the first calculation module 40, and the calculated heartbeat interval calculated by the second calculation module 42, and determines whether or not the period for which the feature value of the pulse wave velocity and the calculated heartbeat interval were calculated is a specified stable interval (parameter determining interval). And, the biosignal-measuring device 1, if the third calculation module 44 determines that it is not a parameter determining interval (S104: No), proceeds with the process at S106. The biosignal-measuring device 1, if the third calculation module 44 determines that it is the parameter determining interval (S104: Yes), proceeds with the process at S108.

At step 106 (S106), the third calculation module 44, applying the current parameters, calculates the relational expression (e.g., determining a functional relationship between the feature value and the heartbeat interval) between the feature value (which is a mathematical manipulation of the pulse wave velocity value) and the heartbeat interval. Here, the third calculation module 44 uses a retained initial value of the parameter for the calculation of the first relational expression.

At step 108 (S108), the third calculation module 44 calculates the relational regression parameters (e.g., linear regression parameters such as slope and intercept) between the feature value and the heartbeat interval within the parameter determining interval. In other words, the third calculation module 44 updates the relational expression parameters.

At step 110 (S110), the heartbeat interval estimation module 46 estimates the heartbeat interval (estimated heartbeat interval) using the feature value calculated by the first calculation module 40, and the relational expression calculated by the third calculation module 44.

At step 112 (S112), the determination module 48 determines whether or not the difference between the calculated heartbeat interval and the estimated heartbeat interval is over a predetermined threshold continuously for some specified period. If the determination module 48 determines that the difference between the calculated heartbeat interval and the estimated heartbeat interval is not over the threshold (S112: No), the biosignal-measuring device 1, proceeds with the process at S114. In addition, if the determination module 48 determines that the difference between the calculated heartbeat interval and the estimated heartbeat interval is over the predetermined threshold continuously for a specified period (S112: Yes), the biosignal-measuring device 1 proceeds with the process at S116.

At step 114 (S114), the blood pressure calculation module 56 calculates the systolic blood pressure value P using an estimated equation generated by the estimated equation generation module 54, and the blood pressure output module 58 outputs the calculation result as an estimated value of the blood pressure. Here, if the correcting module 52 corrected the relational expression, the biosignal-measuring device 1 outputs the estimated value of the blood pressure that reflects corrected relational expression.

At step 116 (S116), the determination module 48 determines whether or not the parameter of the relational expression with which the heartbeat interval estimation module 46 estimated the estimated heartbeat interval was the initial value. If the determination module 48 determines that the parameter of the relational expression was not the initial value (S116: No), the biosignal-measuring device 1 proceeds with the process at S118. And if the determination module 48 determines that the parameter of the relational expression is the initial value (S116: Yes), the biosignal-measuring device 1 completes the process.

At step 118 (S118), the notification section 50 notifies the subject (or other user) of slippage of the attached position of the first information acquisition module 3-1 or the second information acquisition module 3-2.

Also, the biosignal-measuring device 1 is not limited to the configuration shown in the above embodiment. For example, it can be configured to estimate multiple blood pressure values to enhance the precision in estimating the blood pressure.

Here, a biosignal measuring program executed by the biosignal-measuring device 1 according to this embodiment has a modular construction, including each part (the first calculation module 40, the second calculation module 42, the third calculation module 44, the heartbeat interval estimation module 46, the determination module 48, the correcting module 52, the estimated equation generation module 54 and the blood pressure calculation module 56) described as a separate component or module. But the functions of the modules, sections, and parts of the biosignal-measuring device 1 may be implemented as an integrated or partially integrated form as a software program or a hardware component, or combinations of software and hardware, where applicable.

While certain embodiments have been described, these embodiments have been presented by way of example only, and are not intended to limit the scope of the inventions. Indeed, the embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A biosignal-measuring device, comprising:
a first information acquisition module configured to acquire multiple pulse wave signals from a subject at a first position;
a second information acquisition module configured to acquire multiple electrocardiogram signals from the subject at a second position different from the first position;
a first calculation module configured to calculate multiple pulse wave velocities based on signals acquired by the first information acquisition module and the second information acquisition module;
a second calculation module configured to calculate multiple heartbeat intervals based on the signals acquired by the first information acquisition module and the second information acquisition module;
a third calculation module configured to calculate a relational expression between multiple pulse wave velocities and multiple heartbeat intervals;
a heartbeat interval estimation module configured to estimate multiple estimated heartbeat intervals based on new multiple pulse wave velocities and the relational expression;
a determination module configured to determine whether a position of at least one of the first information acquisition module or the second information acquisition module is changed based on multiple heartbeat intervals and multiple estimated heartbeat intervals; and
an output module configured to output a notification based on the determination of the determination module.

2. The device according to claim 1, wherein the output module is configured to output the notification as an audible signal.

3. The device according to claim 1, further comprising:
a correcting module configured to correct a parameter of the relational expression to estimate a blood pressure using the multiple pulse wave velocities if the determination module determines that the position of at least one of the first information acquisition module or the second information acquisition module is changed.

4. The device according to claim 1, wherein the third calculation module is further configured to calculate the relational expression between multiple pulse wave velocities and multiple heartbeat intervals for a period in which the first information acquisition module and the second information acquisition module are determined to be receiving signals in a stable manner.

5. The device according to claim 1, wherein the determination module is configured to determine the position of the first information acquisition module or the second information acquisition module is changed when a difference between a calculated heartbeat interval and an estimated heartbeat interval is over a specified threshold for a specified time.

6. The device according to claim 5, wherein the determination module is configured to update the specified threshold based on the signals acquired by the first information acquisition module or the second information acquisition module.

7. The device according to claim 1, wherein the first information acquisition module includes a photoplethysmographic sensor.

8. The device according to claim 1, wherein the second information acquisition module includes first and second electrodes for acquiring a biosignal.

9. The device according to claim 1, wherein the first information acquisition module and the second information acquisition module are integrated on a single body unit.

10. The device according to claim 1, further comprising:
an adhesive unit configured to place the first and second information acquisition modules in contact with the subject.

11. The device according to claim 10, wherein the adhesive unit comprises a belt.

12. The device of claim 1, further comprising:
an input module configured to receive input from the subject.

13. A biosignal measurement method, comprising:
acquiring multiple pulse wave signals of a subject at a first position on the subject;
acquiring multiple electrocardiogram signals of the subject at a second position on the subject, the second position being different from the first position;
calculating multiple pulse wave velocities using the pulse wave signals and the electrocardiogram signals;
calculating multiple heartbeat intervals using the pulse wave signals and the electrocardiogram signals;
calculating a relational expression between multiple pulse wave velocities and multiple heartbeat intervals;
estimating multiple estimated heartbeat intervals based on new multiple pulse wave velocities and the relational expression;
determining whether the first position and the second position are changed using the heartbeat intervals and the estimated heartbeat intervals; and
outputting a notification based on the determination of whether the first position and the second position are changed.

14. The method of claim 13, wherein the multiple pulse wave signals are acquired using an optical electric pulse wave sensor.

15. The method of claim 13, wherein calculating the multiple heartbeat intervals includes calculating a feature value of the multiple pulse wave velocities.

16. The method of claim 13, wherein calculating the relational expression involves a linear regression between a feature width value of the pulse wave velocities and the heartbeat intervals.

17. The method of claim 13, further comprising:
updating a parameter of the relational expression from an initial parameter value based on at least one calculated pulse wave velocity.

18. A non-transitory computer readable medium including a biosignal measuring program that when executed in a computer causes the computer to perform steps comprising:
acquiring multiple pulse wave signals of a subject at a first position on the subject;
acquiring multiple electrocardiogram signals of the subject at a second position on the subject, the second position being different from the first position;
calculating multiple pulse wave velocities using the pulse wave signals and the electrocardiogram signals;
calculating multiple heartbeat intervals using the pulse wave signals and the electrocardiogram signals;
calculating a relational expression between multiple pulse wave velocities and multiple heartbeat intervals;
estimating multiple estimated heartbeat intervals based on new multiple pulse wave velocities and the relational expression;
determining whether the first position and the second position are changed using the heartbeat intervals and the estimated heartbeat intervals; and
outputting a notification based on the determination of whether the first position and the second position are changed.

19. The non-transitory computer readable medium of claim 18, wherein calculating the relational expression involves a linear regression between feature width values of multiple pulse wave velocities and multiple heartbeat intervals.

20. The non-transitory computer readable medium of claim 18, wherein the steps further comprise:
outputting a blood pressure value calculated using multiple pulse wave velocities.

* * * * *